United States Patent
Ziegenhagen et al.

(10) Patent No.: US 6,970,620 B2
(45) Date of Patent: Nov. 29, 2005

(54) WAVEGUIDE FOR RECEIVING AND/OR RADIATING ELECTROMAGNETIC RADIATION

(75) Inventors: Lars Ziegenhagen, Bremen (DE); Gereon Hüttmann, Lübeck (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 10/407,059

(22) Filed: Apr. 3, 2003

(65) Prior Publication Data

US 2003/0190120 A1 Oct. 9, 2003

(30) Foreign Application Priority Data

Apr. 4, 2002 (DE) .......................................... 102 14 811

(51) Int. Cl.[7] .............................................. G02B 6/26
(52) U.S. Cl. ............................. 385/31; 385/39; 606/16
(58) Field of Search .......................................... 385/39

(56) References Cited

U.S. PATENT DOCUMENTS

| | | | | |
|---|---|---|---|---|
| 4,547,233 A | * | 10/1985 | Delzant | .......................... 149/2 |
| 5,074,632 A | | 12/1991 | Potter | ............................ 385/31 |
| 5,119,461 A | | 6/1992 | Beyer et al. | ................. 385/147 |
| 5,190,536 A | | 3/1993 | Wood et al. | ................. 128/398 |
| 5,196,005 A | | 3/1993 | Doiron et al. | ................. 606/16 |
| 5,754,717 A | * | 5/1998 | Esch | ............................ 385/31 |
| 6,096,030 A | | 8/2000 | Ortiz | ............................. 606/14 |
| 6,270,492 B1 | | 8/2001 | Sinofsky | ....................... 606/15 |
| 6,522,806 B1 | * | 2/2003 | James et al. | ................... 385/31 |
| 2002/0072676 A1 | * | 6/2002 | Afanassieva | ................. 600/473 |

FOREIGN PATENT DOCUMENTS

| | | | |
|---|---|---|---|
| DE | 77 06 786 | 6/1977 | ............. G02B/5/14 |
| DE | 39 01 931 | 8/1990 | ............. A61N/5/06 |
| DE | 43 29 914 | 3/1995 | ............. G02B/6/00 |

OTHER PUBLICATIONS

Shortley and Williams, "Elements of Physics For Students of Science and Engineering," (Second Edition, 1955, NY–USA), pp. 466–467.

* cited by examiner

Primary Examiner—John R. Lee
Assistant Examiner—Philip A. Johnston
(74) Attorney, Agent, or Firm—Cohen, Pontani, Lieberman & Pavane

(57) ABSTRACT

In the region of a distal end at its circumference the waveguide is formed transparent to the radiation which impinges onto the surface of the waveguide at suitable angles, and in the region of the distal end in the inside of the waveguide there are arranged scatter elements which scatter radiation transmitted by the waveguide in the direction of the distal end in a direction with a proximally directed component which exits the circumference of the waveguide. Alternatively, radiation entering into the waveguide at the circumference of the waveguide in a direction with a distally directed component is transmitted by the waveguide in the direction of the proximal end, as well as to its use and to a method for its manufacture.

18 Claims, 3 Drawing Sheets

WAVEGUIDE FOR RECEIVING AND/OR RADIATING ELECTROMAGNETIC RADIATION

PRIORITY CLAIM

Priority is claimed for this invention and application, a corresponding application having been filed in Germany on Apr. 4, 2002, No. 102 14 811.2.

BACKGROUND OF THE INVENTION

1. Field of the Invention

The invention relates to a waveguide for receiving or radiating electromagnetic radiation, in particular light, to the use of such a waveguide as well as to a method for manufacturing such a waveguide.

2. Description of the Related Art

For a series of technical and medical uses it is necessary to uniformly illuminate a cavity. For spherical cavities this may be effected by an isotropic radiation source which is located in the center of the cavity. If the radiation source may not or is not to be brought itself into the cavity, such as e.g. with the examination and therapy of hollow organs in the human body, an optical waveguide which is provided at its end with an isotropically radiating scatter body may guide the light or the radiation from the source into the inside of the cavity and here radiate isotropically.

One example of the use of such a device for the uniform illumination or radiation of the inner surface of a spherical human hollow organ is integral photodynamic therapy (PDT) in a urinary bladder with multifocal tumor occurrence. For the success of this therapy it is necessary e.g. for the inner wall of the urinary bladder which is stabilized in spherical manner to be radiated homogeneously. A non-homogeneous intensity distribution of the light radiation directed onto the inner wall of the urinary bladder at locations with a low radiation dose leads to no or an inadequate destruction of the photo-sensitivised tumour tissue.

All isotropically radiating scatter bodies known up to now have a ball of light-scattering material located at the end of an optical waveguide. See, for example, U.S. Pat. Nos. 5,119,461; 5,074,632; 5,190,536; and 6,096,030. With this known device, hereinafter called an applicator, the photons in the ball exiting the optical waveguide are scattered many times in a diffuse manner so that they lose their original direction. With a suitable choice of the composition of the scatter medium, this leads to approximately spherical radiation characteristics of the applicator. In order to also radiate sufficient light intensity in the direction of the optical waveguide, i.e. in the proximal direction and thus to reduce shadowing effects by way of the optical waveguide, the ball diameter of the scatter body is about four times larger than the diameter of the optical waveguide. This entails the following disadvantages.

The constructional shape of the known applicator, at the connection location of the optical waveguide to the spherical scatter body particularly with small applicator sizes creates problems with regard to the mechanical stability. Furthermore the diameter of the optical waveguide limits the maximum power which may be transmitted into the cavity. With spatially incoherent radiation the ability to focus is limited and only a sufficiently large optical waveguide permits an effective transmission of the light. With laser radiation which on account of its coherence and monochromatic property may be focussed very well, the destruction threshold of the optical waveguide or the connection of this to the scatter body limits the transmittable power. In both cases the power able to be transmitted by the optical waveguide increases with its cross-sectional area. It is therefore desirable to adapt the diameter of the optical waveguide as much as possible to the respective cavity diameter or access channel to the cavity. With the scatter bodies of the applicators described in the state of the art which guarantee a largely homogeneous illumination of the cavity, the diameter of the guiding optical waveguide is limited to a quarter of the diameter of the scatter body and thus of the diameter of the access to the cavity.

In medicine and technology spherical or similar cavities may be reached only via a relatively small access channel. With the above-mentioned photodynamic therapy (PDT) of the urinary bladder, the diameter of the spherical scatter body of the applicator should be $\leq 3$ mm on account of the narrow urethra. At the same time with the applicator of the state of the art the diameter of the optical waveguide would have to be limited to $\leq 0.75$ mm. By way of the thus relatively low optical waveguide cross section and by way of the high scatter coefficients of the scatter body, already with relatively low laser powers of $\leq 3$ W at the exit area of the optical waveguide there occur such high radiation intensities that the heating produced with this may lead to a destruction of the applicator.

DE 3 941 705 C2 describes a device for the homogeneous radiation of cavities which consists of a balloon catheter in which the conically pointed end of the optical waveguide is positioned centrically to the middle of the balloon in the catheter. The balloon is filled with a diffusely scattering liquid and at the same time assumes a spherical shape. Since the actual applicator only first appears at the user on filling the balloon, there lacks an exact quality control with regard to the quality of the radiation characteristics of the radiation applicator. For the user it is also cumbersome and difficult to fill the balloon with absolutely no bubbles. Furthermore the balloon may be perforated on introduction into the cavity. Since yet an additional channel must be provided for filling, and the balloon takes up some space even in the non-filled condition, here too one may not use the complete diameter of the access channel for the diameter of the optical waveguide.

SUMMARY OF THE INVENTION

With regard to the disadvantages of the state of the art it is the object of the invention to provide a waveguide for receiving and/or radiating electromagnetic radiation, in particular light, with universal radiation and receiving characteristics, which with small dimensions permits the transmission of a high power. A further object of the invention is to provide a method for manufacture of such a waveguide.

The waveguide according to the invention for receiving and/or radiating electromagnetic radiation, in particular light, in the region of its distal end on its circumference is formed transparent to the radiation which impinges the surface of the waveguide at suitable angles. The distal end of the waveguide is that end which is used for radiation or receiving the light and for example is introduced into a hollow organ of a human body. The transparency to the radiation in this region is designed such that it is only limited by the critical angle of the total reflection. For this the difference of the refractive indices between the waveguide and the surroundings, usually air, is selected as low as possible in order to ensure a large transparency to the radiation. The lower limit for the refractive index difference is defined by way of the fact that the radiation-guiding properties of the waveguide must not be lost. This means that the refractive index difference must be selected such that radiation which is introduced into the waveguide at the proximal end at a predefined angle must be transmitted by this in as loss-free manner as possible. Radiation which however impinges the surface of the waveguide at a greater angle than this critical angle, may exit or enter the waveguide at least at the circumference in the region of the distal end.

Furthermore scatter elements are arranged in the inside of the waveguide in the region of its distal end in a manner such that radiation transmitted from the waveguide in the direction of the distal end is deflected or scattered at least in part in a direction with a proximally directed component and exits at the circumference of the waveguide out of this. This means the radiation is scattered in a manner such that it is thrown back and is deflected through the waveguide into the rearward space. In this manner by way of the arrangement of the scatter elements in the inside of the waveguide and by way of the radiation-permeable design of the surface of the waveguide one may achieve spherical or isotropic radiation characteristics. At the same time the maximum outer circumference of the radiation-emitting element is defined by the outer circumference or outer diameter of the waveguide. It is no longer necessary to provide a scatter body larger in diameter in order to illuminate or radiate the space which is rearwards or proximal with respect to the distal end of the waveguide. Thus the diameter of the waveguide may be enlarged to a maximum which is limited by the size of an access channel to a cavity, for example in the human body. In this manner the transmission of radiation with a greater power is possible without a damage or destruction occurring to the light guide.

On the one hand, as described, the waveguide according to the invention may be used as a radiation source which emits radiation to the outside. On the other hand the waveguide in a reverse manner may however also be used for receiving electromagnetic radiation, wherein it forms a sensor with isotropic sensitivity. When receiving electromagnetic radiation, radiation which in a direction with a distally directed component enters the waveguide at its circumference, radiation is deflected or scattered in the waveguide by the scatter elements in a manner such that the radiation is transmitted through the waveguide in the direction of the proximal end. This means that the radiation which impinges the surface of the waveguide at an acute angle enters the circumferential region transparent to the radiation into the waveguide and is deflected or scattered by the scatter elements arranged in the inside of the waveguide in a manner such that it is thrown back in the proximal direction and transmitted through the waveguide in the proximal direction. Thus the waveguide according to the invention may for example be applied as a sensor or observation element.

Preferably at least part of the scatter elements are formed in the inside of the waveguide. Such scatter elements may be produced in the inside of the waveguide in various manners. For example scatter elements in the form of balls may be arranged in a directed manner at predefined locations in the inside of the scatter body.

In a preferred embodiment form, at the distal end of the waveguide there is formed a concave holder into which a corresponding scatter body is fitted in a manner such that the scatter body at least partly is arranged in the inside of the waveguide, wherein the scatter elements are formed on or in the scatter body. The concave holder is preferably arranged at the distal end face side of the waveguide—this separate formation of the scatter body and the waveguide permits a simpler manufacture of the waveguide since the scatter body with the scatter elements may be manufactured separately and then applied on the distal end of the waveguide. The diameter or outer circumference of the scatter body preferably has a maximal size which is equal to or smaller than the outer diameter of the waveguide. In this manner it is ensured that also with this embodiment form the maximal outer dimensions of the waveguide are defined by its diameter and not by the scatter bodies.

Preferably the scatter body is formed of a material which is transparent to the electromagnetic radiation and at least part of the scatter elements are arranged in the inside of the scatter body. At the same time the scatter elements may be positioned in the inside of the scatter body in a targeted manner in order to produce predefined scatter characteristics. One sets scatter or deflection characteristics of the scatter body which ensure a sufficient illumination of the space which is proximal with respect to the distal end of the waveguide. The radiation scattered by the scatter elements in the scatter body at the distal end again enters the waveguide and then exits this at its outer circumference. On exit at the outer circumference of the waveguide which is formed transparent to the radiation, the radiation is furthermore preferably additionally refracted in the proximal direction of the waveguide so that the space on the proximal side in the circumference of the waveguide may be adequately radiated and no shadowing by the waveguide occurs.

Furthermore the scatter body may be formed of a material which is transparent to the radiation to be transmitted and at least part of the scatter elements may be arranged on the surface of the scatter body. This design permits a simple manufacture of the scatter body, since the individual scatter elements may be arranged in a relatively simple and defined manner on the surface of the scatter body.

Preferably the scatter elements are arranged at least on one proximal surface of the scatter body between the scatter body and the holder in the waveguide. By way of this arrangement it is ensured that a part of the electromagnetic radiation which is radiated from the waveguide in the direction of the scatter body is scattered or deflected by the scatter elements arranged between the scatter body and the waveguide. The radiation is thrown back into the waveguide by the scatter elements and deflected such that it exits the waveguide at the radiation-transparent circumferential surface of the waveguide.

At least part of the scatter elements are further preferably distributed over the whole surface of the scatter body. This means part of the scatter elements are also arranged at the distal side of the scatter body which is distant to the distal end of the waveguide. These scatter elements ensure a scattering of the radiation radiated from the scatter body. At the same time a part of the radiation is also thrown back into the inside of the scatter body and the waveguide that it exits the radiation-transparent circumferential surface of the waveguide in the proximal direction or in a direction with a proximal component. By way of a targeted and defined arrangement of the individual scatter elements on the surface of the scatter body one may produce predefined radiation characteristics of the scatter body, in particular spherical or isotropic radiation characteristics. Apart from isotropic radiation characteristics one may for example produce elliptical radiation characteristics. It is possible to produce almost any radiation characteristics by way of a defined arrangement of the scatter elements since on account of the arrangement of the scatter elements according to the invention one also achieves an illumination of the proximal space.

A lower number of scatter elements may be distributed on the proximal surface of the scatter body than on the distal surface. By way of a greater concentration of scatter elements on the distal surface, part of the radiation is thrown back into the inside of the scatter body and the inside of the waveguide and may then exit in the proximal direction at the radiation-transparent circumferential surface of the waveguide.

It is further preferred for a larger number of scatter elements to be distributed in a circumferential or equatorial surface region between the distal surface and the proximal surface of the scatter body than in the remaining surface regions. The isotropic radiation of the electromagnetic radiation is improved by way of this arrangement. The number of applied scatter elements is proportional or synonymous to the intensity or extent of the produced radiation.

The scatter body is preferably formed spherical and the concave holder is preferably formed as a hemispherical shell. At the same time the hemispherical shape of the concave holder corresponds to the shape of the scatter body. In this manner almost half of the spherical scatter body is accommodated in the inside of the holder. The isotropic radiation of the scatter body and of the distal end of the waveguide is further encouraged by the spherical design of the scatter body. Depending on the field of application, for example if different radiation characteristics are desired, one may also apply a non-spherical scatter body. For example an egg-shaped or spherical or conical shaping of the scatter body is conceivable, wherein the holder in each case is shaped correspondingly.

The scatter elements are usefully distributed in a manner such that at least 50% of the radiation transmitted by the waveguide is scattered with a proximally directed component. This means half the radiation is scattered or deflected by the scatter elements in a manner such that they are thrown back at an acute angle to the longitudinal axis of the waveguide. The radiation then exits the waveguide at the radiation-transparent circumferential surface of the waveguide and on account of the difference in refractive index to the surroundings is additionally refracted towards the longitudinal axis of the waveguide. In this manner one may achieve a good illumination of the rearward or proximal region. Thus one may achieve the desired isotropic or uniform radiation.

Preferably the previously described waveguide is designed as a light guide for transmitting light. For example laser light for radiating tissue may be transmitted through the light guide.

The waveguide is preferably formed of glass or quartz. At the same time the waveguide usefully has a rod-like shape of an essentially circular cross section. Glass or quartz permit a largely loss-free transmission of light. The surface of the waveguide up to the region at the distal end of the waveguide which is permeable to the radiation is preferably provided with a cover layer opaque to the radiation. In this manner the ability of the waveguide to conduct radiation and light is further improved.

The scatter elements preferably comprise gas-filled glass elements and in particular gas-filled glass beads. Such glass elements or glass beads may in particular be deposited onto the surface of the scatter body. They may be arranged on the surface of the scatter body in a very targeted and defined manner in order to produce predetermined defined scatter characteristics of the scatter body.

At least one partly or fully reflecting layer for deflecting the radiation may be provided in the region of the distal end of the waveguide. Such a layer may for example also be deposited onto the surface of a scatter body. The reflecting layer may be deposited on the border layer between the waveguide and the scatter body. This layer has the effect that at least a part of the radiation is reflected and thrown back into the inside of the waveguide so that if it impinges the radiation-transparent surface of the waveguide at a suitable angle, it may exit this surface. The deflection of the radiation in the proximal direction or in a direction with a proximal component may thus be increased at least one partly or fully reflecting layer for deflecting the radiation in order to further improve the illumination of the space on the proximal side.

Furthermore it is possible to provide refractive index variations in the region of the distal end for deflecting the radiation. It is possible to form elements or regions with different refractive indices in the inside of the waveguide or on the surface or in the inside of the scatter body. In this manner one may produce a targeted deflection of the radiation in order in particular to achieve ideal isotropic radiation characteristics.

The spatial arrangement of the scatter elements or regions which a changed refractive index as well as their dimension is preferably greater than the wavelength of the radiation to be transmitted. By way of this it is achieved that the deflection of radiation is largely independent of the wavelength of the radiation.

The invention further relates to the use of a waveguide with the previously described design as an applicator for medical purposes. The described waveguide may in particular be used for radiating hollow organs. For example the waveguide according to the invention may for example be used for integral photodynamic therapy (PDT) in a urinary bladder. The waveguide is suitable for such an application since almost isotropic radiation characteristics may be achieved with it, without having to provide scatter bodies which have larger dimensions than the outer diameter of the waveguide. It is possible in this manner to transmit large radiation intensities or powers through relatively narrow accesses into the inside of hollow organs.

The constructional shape of the applicator is preferably rod-like and has no parts which are larger than the diameter of the light-guiding or radiation guiding elements, i.e. of the optical waveguide. Thus the applicator and all relevant elements of an associated diagnosis and therapy apparatus may be maximally adapted to the respective cavity access channel which in particular with radiation with relatively poorly focusable radiation sources, such as light-arc lamps, reduce in-coupling and transmission losses to as great as minimum as possible. The radiation characteristics of the applicator may be set by way of a suitable shaping and coating of the scatter body. In this manner applicators may be manufactured which e.g. radiate chiefly to the front, to the side or back, i.e. in the proximal direction. The applicator due to its compact constructional shape is mechanically very stable and is easy to handle.

With an alternative method for manufacturing the waveguide according to the invention one envisages the following steps. Firstly on the distal end of the waveguide there is formed a concave holder. At the same time the holder preferably forms a recess at the distal end-face of the waveguide. Furthermore one provides a scatter body which comprises as least one convex surface section with a shape corresponding to the holder. As a next step a curable adhesive is deposited onto at least the convex surface section and/or the holder. Materials which have good optical properties or a suitable radiation permeability are particularly. The adhesive should preferably have a similar refractive index to the bordering waveguide and scatter body. Epoxide resins or adhesives based on acrylic are for example suitable.

As a next step scatter elements are incorporated into the adhesive on at least the convex surface section and/or the holder. At the same time the individual scatter elements may be arranged at predefined positions in order to exactly set the scatter characteristics. The scatter elements are subsequently embedded in the adhesive so that no further border surfaces or interruptions are present which could compromise the radiation transmission. Subsequently the scatter body with its convex surface section is applied into the holder, wherein the adhesive preferably creates a rigid connection between the scatter body and the waveguide. Depending on the adhesive used, the adhesive material may subsequently be cured for example by ultraviolet radiation or heat. After completion of this method the individual scatter elements in the adhesive are arranged in the border layer between the scatter body and the waveguide. Furthermore the waveguide is designed such that in the region of its distal end the circumferential surface is transparent to radiation. For this the circumferential surface of the optical waveguide is designed in a manner such that it has good optical surface properties. In particular the waveguide in this region is provided with a radiation-opaque coating. With the use as a light guide in particular glass or quartz are suitable as material for the waveguide. However also suitable plastics, for example acrylic glass may be used. The material selection in particular depends on the wavelength of the radiation to be transmitted. Thus for example also silicon may be suitable for radiation in the infra-red region.

The scatter elements are preferably gas-filled glass elements and in particular gas-filled glass beads. A defined scattering may be achieved with such scatter elements. Furthermore these scatter elements may be relatively easily attached onto the scatter body surface in a defined manner. They may be scattered onto the surface in the desired regions which have previously been provided with adhesive, or placed on individually.

In a method variant the adhesive and the scatter elements may be deposited onto the whole surface of the scatter body, so that the scatter elements are not arranged only in the border layer between the scatter body and the waveguide. One may set the radiation characteristics more accurately by way of the distribution of scatter elements over the whole surface of the scatter body. It is possible to arrange the scatter elements at various regions of the surface in different concentrations.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

It is to be mentioned here that for the description of the device one has used two-dimensional representations, as with the above-listed figures, since with the described device there is rotational symmetry.

Figure 1A:
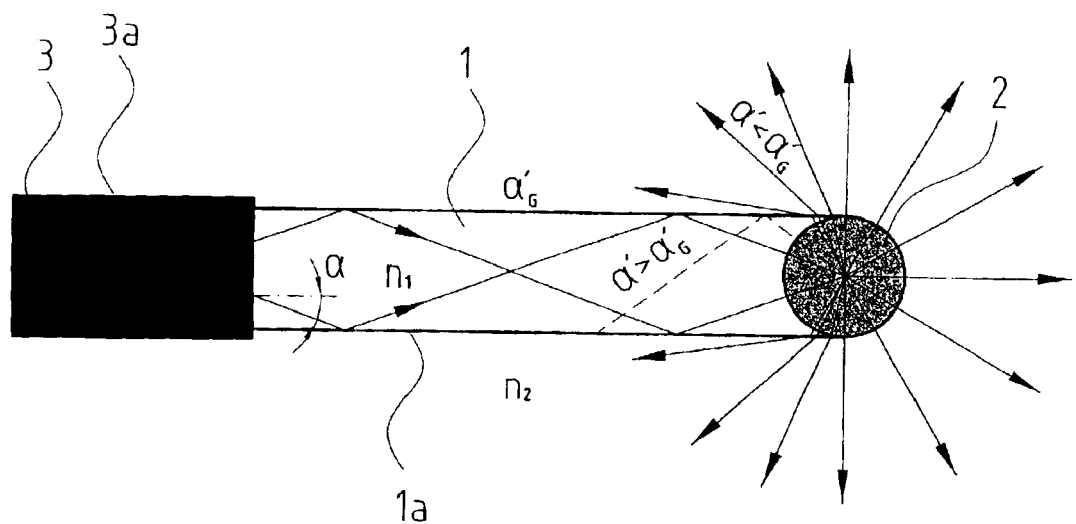
FIG. 1a a basic representation with selected beam paths for explaining the construction and the function of the device according to the invention, FIG. 1b enlarged, a possible radiation course with rearward scattering in the scatter body, FIG. 2 graphically, a diagram for explaining the radiation characteristics of the device, FIG. 3 schematically, one embodiment example of a device according to the invention for radiating spherical cavities, and FIG. 4a further embodiment example with which the scatter body is arranged further distanced from the distal end of the waveguide.

FIG. 1a in principle shows the construction and manner of functioning of the device according to the invention. This consists of a waveguide 1 which is transparent to the radiation to be transmitted. Preferably it is the case of a light guide or optical waveguide, e.g. a glass, quartz or acrylic-glass rod. Furthermore the device includes a scatter body 2 which diffusely scatters the radiation, in particular light and which is fastened at the distal end of the optical waveguide 1. The optical waveguide 1 and the scatter body 2 form an applicator which may either be connected directly to a suitable light source or via a further optical waveguide 3, wherein the light-guiding core of the optical waveguide 3 may be formed as one piece with the optical waveguide 1. The scatter body 2 has a smaller or equal diameter as the optical waveguide 1 and is partly arranged in the inside of this.

The optical waveguide 3 on its outer circumference is surrounded by a radiation-opaque or light-opaque casing which improves the transmission properties of the optical waveguide 3. The optical waveguide 1 forms the core of the optical waveguide 3, wherein the casing 3*a* is removed or not deposited in the region of the optical waveguide 1, in order to create the radiation-permeable or light-permeable surface 1*a*.

Figure 1B:
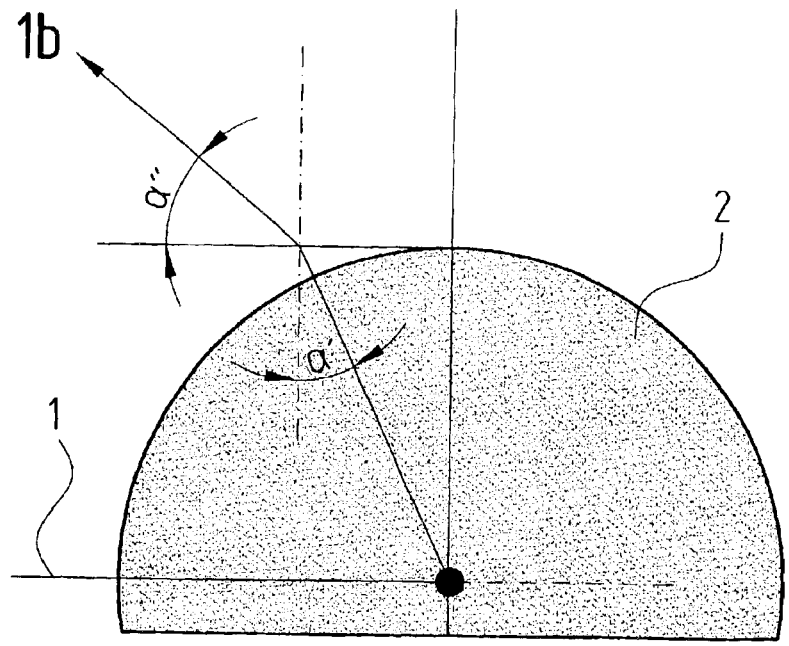

Radiation or light enters the optical waveguide 1 at an angle $\alpha$ to the longitudinal axis of the optical waveguide 1. If one selects the material of the optical waveguide 1 such that its refractive index $n_1$ is larger than the refractive index $n_2$ of the surrounding medium, then radiation which propagates at an angle $\alpha < \alpha_G$ in the optical waveguide 1 is completely reflected on its walling. The following is applicable for the critical angle $\alpha_G$:

$$\alpha_G = \frac{\pi}{2} - \arcsin\left(\frac{n_2}{n_1}\right) \quad (1)$$

wherein $n_1$ is the refractive index of the optical waveguide 1 and $n_2$ is the refractive index of the surrounding medium. If now when in-coupling light it is ensured that the entering light beams do not exceed the critical angle $\alpha_G$, the optical waveguide 1 transmits the coupled-in light to the scatter body in an almost loss-free manner, wherein essentially no refraction occurs between the optical waveguide 1 and the scatter body 2. The scatter body 2 diffusely scatters the light in all spatial directions. If the scattering at the scatter body 2 is e.g. effected isotropically, as is shown in FIG. 1*a*, then in the forwards direction the radiation intensity is isotropically distributed over the front hemisphere. In the direction of the rear hemisphere, i.e. towards the proximal direction, scattered photons or beams are again coupled into the optical waveguide 1 (FIG. 1*b*) and according to the angle $\alpha'$ at the wall of the optical waveguide is totally reflected ($\alpha' > \alpha_G$) or is refracted at the border layer of the optical waveguide 1 to the surrounding medium ($\alpha < \alpha_G'$, wherein $\alpha_G' = 180E - \alpha_G$). In the first case the photons for radiation of the rear hemisphere are lost. In the second case the photons leave the optical waveguide 1 at the circumferential surface 1*a* at an angle $\alpha''$ with respect to its longitudinal axis:

$$\alpha'' = \frac{\pi}{2} - \arcsin\left(\frac{\sin(\frac{\pi}{2} - \alpha') \times n_1}{n_2}\right) \quad (2)$$

wherein $\alpha''$ specifies the angle between the light radiation leaving the optical waveguide 1 and the longitudinal axis of the device, $\alpha'$ the angle between the photon or beam path in the optical waveguide 1 and a normal standing on its longitudinal axis, $n_1$ the refractive index of the optical waveguide 1 and $n_2$ the refractive index of the surrounding medium. In order to permit the exit of light from the optical waveguide 1, this in its circumferential region 1*a* is designed transparent to the radiation to be transmitted, i.e. to light.

From this equation (2) one may derive the following important feature of the device according to the invention: if $n_1 > n_2$, the radiation scattered back at the scatter body, with $\alpha' > \alpha_G'$ at the border surface of the optical waveguide 1 to the surrounding medium, is refracted into the whole rear half solid angle. This is true independently of the size of the ratio of the refractive index $n_1/n_2$.

Figure 2:
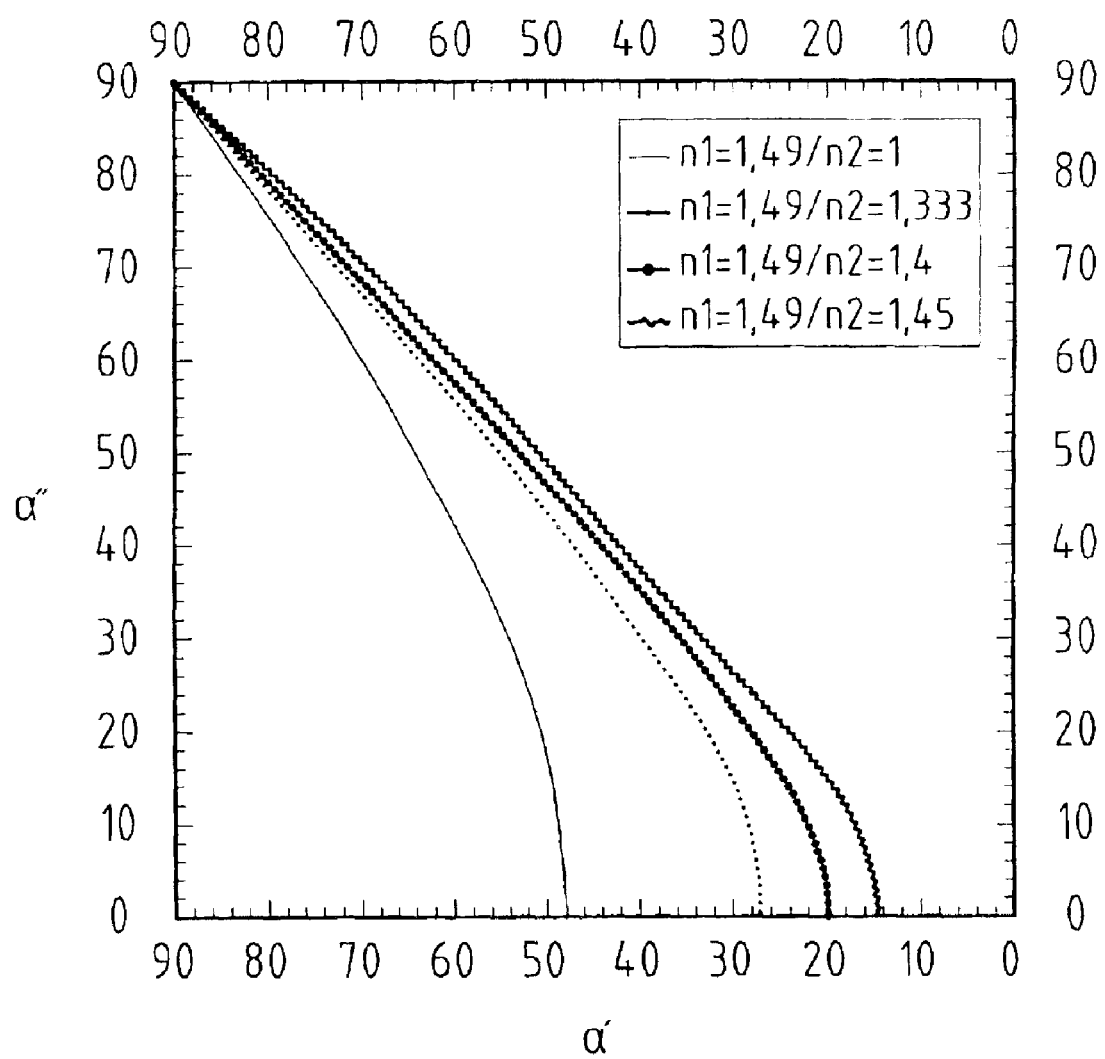

By way of four examples in each case with different ratios of the refractive index $n_1/n_2$, FIG. 2 illustrates the relationship between the angles $\alpha'$ and $\alpha''$, wherein in this example for the refractive index $n_1$ one has assumed the refractive index of acrylic glass ($n_1 = 1.49$). The curves in FIG. 2 run linearly for larger angles. If the angle $\alpha''$ approaches the critical angle $\alpha_G$, $\alpha''$ increases more than $\alpha'$. With isotropic backward scattering then for a larger $\alpha'$ one obtains an almost isotropic distribution of intensity. Although light is lost by Fresnel reflection depending on the angle $\alpha'$, with this arrangement with an isotropic light distribution by the scatter body 2 one may also achieve quite a uniform illumination in the rearward or proximal direction.

Due to the non-linearity of the refraction law which is not reflected by the curves in FIG. 2, the light is distributed over a larger angle and the radiation intensity in the rearward scatter region of the device as a whole is reduced by the factor $n_2/n_1$.

With a reducing difference of refractive index the critical angle for the total reflection also becomes smaller, by which means the component of scattered-back light which leaves the device in the direction of the rear hemisphere, i.e. towards the proximal direction, increases.

For as homogeneous as possible intensity distribution of the whole rear hemisphere and in order to keep the intensity losses of the device as small as possible it is therefore useful to keep the refractive index difference between the optical waveguide 1 and the surrounding medium as low as possible, wherein however the critical angle $\alpha_G$ may not exceed the angle with which the coupled-in radiation propagates in the optical waveguide 1, since otherwise the optical waveguide 1 of the device would lose its properties as an optical waveguide which were described at the beginning. In any case a part of the light which is scattered into the rearwards hemisphere is lost due to reflection at the casing of the optical waveguide 1, so that a rearward or proximal region or distal region is illuminated more weakly than a front region. This may, as Monte-Carlo computations and experiments have shown, be compensated by an asymmetrical design of the scatter properties of the scatter body 2.

Figure 3:
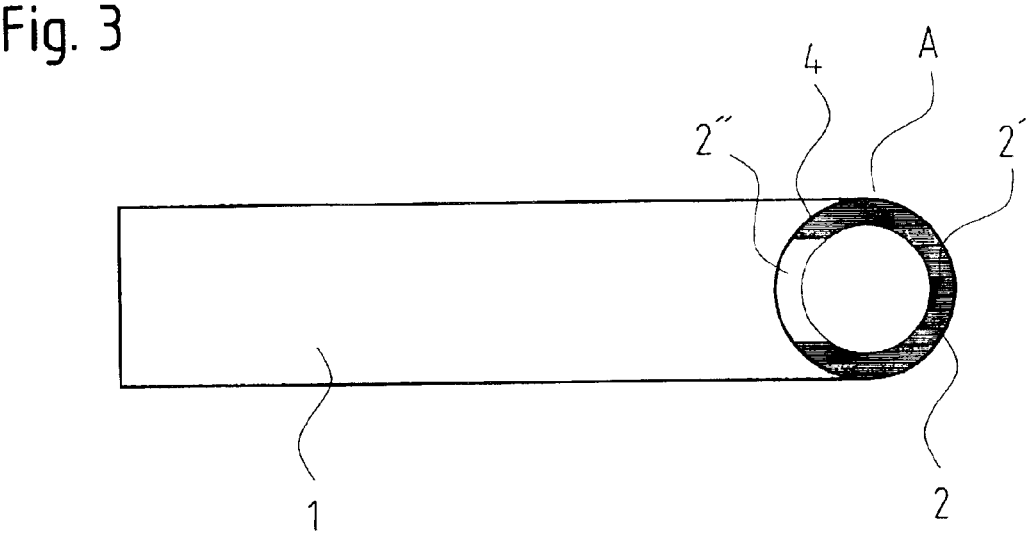

In FIG. 3 there is shown a practical realization of a device according to the invention for radiating spherical cavities. For the device one may use an optical waveguide 1 in the form of an acrylic glass rod or glass rod with a suitable length and fitting diameter. One end of the optical waveguide 1 has a concave-hemispherical recess 4 into which a scatter body 2 with a suitable size formed of two hemispherical shells 2', 2" is held. According to the invention the scatter body 2 has a diameter which is equal in size or smaller than the optical waveguide 1. The two transparent hemispherical shells 2' and 2" are doped with diffusely scattering materials, such as e.g. BaSO$_4$ or TiO$_2$ or gas-filled glass balls. The extent of the doping is represented in FIG. 3 by way of example as a grey tinge. The reflectivity of both hemispherical shells 2', 2" and thus the radiation characteristics may be set by way of the extent of doping. The regions of the hemispherical shells 2', 2" which are shown darker in FIG. 3 are doped more intensely than the lighter represented regions. In particular the distal hemispherical shell 2' is doped more intensely than the proximal half shell 2". Thus the edge region of the hemispherical shells 2' and 2" circumferentially with respect to the longitudinal axis of the optical waveguide 1 is more intensely doped than in remaining regions. In this manner in the distal and circumferential region of the scatter body 2 a greater scattering is produced so that as isotropic as possible radiation characteristics may be achieved.

It has been shown experimentally that e.g. for approximately spherically symmetrical radiation characteristics the reflectivity of the hemispherical shell 2" in the region to the rear hemisphere, i.e. in the proximal direction, must be double as large in order to match radiation intensities in the distal and proximal direction. One obtains the best results if the doping of the hemispherical shells 2' and 2" at the same time is not uniform, but e.g. increases towards the equator A. By way of this the intensity distribution of the laterally radiated light is optimized.

By way of a suitable shaping and doping of the scatter body 2 one may also manufacture a device according to the invention with approximately elliptical radiation characteristics. One may likewise also manufacture a device according to the invention which chiefly radiate in the distal direction, lateral direction or in the proximal direction.

If scatter particles whose diameter is considerably larger than the wavelength are embedded into the scatter body 2 then the scatter properties of the scatter body are largely independent of the wavelength, and the scatter body may then be applied for multi-colored light. This may very effectively be achieved by embedding air-filled glass balls with a diameter of a few to 10 μm which are embedded into a light-transparent medium of the scatter body 2.

The design of the scatter body 2 with two hemispherical shells 2' and 2" is described in FIG. 3. Alternatively the scatter body may be formed as a transparent ball which is shaped corresponding to the recess 4. A curing or curable material, for example an adhesive may be deposited over the whole surface or also only on the surface region facing the recess 4, and in this material are embedded the scatter elements as for example the previously described glass beads. These scatter elements may be arranged in different concentrations on the various regions of the surface of the scatter body in order to achieve the previously mentioned scatter characteristics. Instead of an intense doping according to the preceding embodiment example, in this case in the corresponding regions a larger number of scatter element or glass beads are arranged in order to achieve an increased scattering. In the previously described embodiment examples the scatter body 2 in each case is designed spherically. It is however also conceivable to design the scatter body with a different shape, wherein then advantageously the recess 4 in the optical waveguide 1 has a corresponding shape. For example the scatter body 2 may have an elliptical cross section and the recess 4 may have a corresponding concave shape. Instead of arranging the scatter elements on the surface of the scatter body the scatter elements may also be formed or arranged in the inside of the scatter body.

Instead of designing the scatter body 2 as a separate component from the optical waveguide 1, scatter elements may also be arranged directly in the inside of the optical waveguide 1. For this it is possible to arrange suitable scatter particles in the inside of the waveguide 1 in a suitably targeted manner in order to achieve a scattering into the rearward or proximal space of the optical waveguide 1. In particular it is possible likewise to arrange the scatter particles or scatter elements essentially in a spherical distribution in the inside of the optical waveguide 1, so that a distribution is achieved according to the previously described examples.

Figure 4:
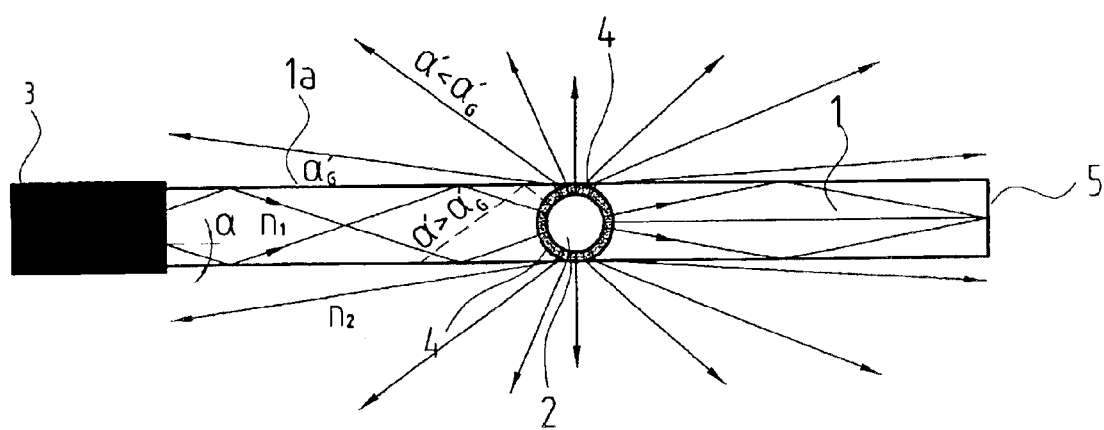

FIG. 4 shows a further example of the optical waveguide according to the invention. The covered optical waveguide 3 and the optical waveguide 1 correspond essentially to the optical waveguides described in the previous embodiment examples. The optical waveguide 3 is provided with a non-transparent casing, whilst the optical waveguide 1 which is preferably formed as one piece with the core of the optical waveguide 3 has a radiation-permeable or light permeable surface 1a. In contrast to the optical waveguide 1 shown in FIG. 1a and FIG. 3, in FIG. 4 the scatter body 2 is not arranged at the distal end of the optical waveguide 1 but in a middle region. For this the optical waveguide 1 is preferably formed in two parts, wherein in each of the two parts there is formed a corresponding concave recess 4 in which the scatter body is held. The scatter body 2, as explained by way of FIG. 3 may consist of two hemispherical shells or be formed as a transparent spherical body with deposited or incorporated scatter elements. The distal end 5 of the optical waveguide 1 is preferably designed reflecting, so that the radiation or light beams are reflected from this end face 5 back to the scatter body 2 and are scattered outwards by this. In this embodiment form too the light beams deflected or scattered in the proximal direction by the scatter body 2 are again coupled into the optical waveguide 1 and exit through the circumferential surface 1a in the proximal direction or in a direction with a proximal component. In the distally situated half of the optical waveguide 1 the light beams reflected by the end face 5 are likewise deflected by the scatter body 2 so that they again are coupled into the optical waveguide 1 in the distal direction or a direction with a distal component and exit the circumferential surface 1a.

The device according to the invention, as has been described above may not only be used for illuminating or radiating cavities. With this it is also possible to design a radiation sensor, e.g. light detector with spatially isotropic sensitivity, if a radiation sensor such as e.g. a photodetector is placed at the proximal end of the optical waveguide instead of a light source. Furthermore it is to be noted that the device according to the invention is also suitable for non-visible electromagnetic radiation.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A waveguide for at least one of radiating and receiving electromagnetic radiation, said waveguide comprising a central axis, a circumferential surface which is concentric to said axis and is transmissive only to radiation which impinges said surface at angles greater than a critical angle of total reflection in the waveguide, a distal end defining a proximal direction extending axially away from said distal end, said circumferential surface extending to said distal end, said distal end having a concave spherical surface, and a spherical scatter body fitted into said concave spherical surface, said scatter body having scatter elements arranged at said distal end at least one of on and in said scatter body so that at least one of the following transpires:

radiation transmitted by the waveguide toward the distal end is scattered by the scatter elements at least in part in a direction with a proximal component and exits the circumferential surface, and radiation entering the circumferential surface of the waveguide in a direction with a distal component is transmitted by the waveguide at least in part in the proximal direction.

2. A waveguide as in claim 1 wherein said scatter body comprises a material which is transparent to electromagnetic radiation, at least part of said scatter elements being arranged inside said scatter body.

3. A waveguide as in claim 1 wherein said scatter body is founed of a material which is transparent to radiation to be transmitted, at least part of said scatter elements being arranged on the surface of said scatter body.

4. A waveguide as in claim 3 wherein at least part of said scatter elements are arranged between the scatter body and the concave surface.

5. A waveguide as in claim 4 wherein at least part of said scatter elements are distributed over the whole surface of the scatter body.

6. A waveguide as in claim 5 wherein said scatter body comprises a proximal surface and a distal surface, more of said scatter elements being arranged on said distal surface than on said proximal surface.

7. A waveguide as in claim 5 wherein said scatter body comprises a proximal surface, a distal surface, and a circumferential surface therebetween, more of said scatter elements being arranged with a greater density on said circumferential surface than on said proximal surface and said distal surface.

8. A waveguide as in claim 1 wherein said scatter elements are distributed so that at least fifty percent of the radiation transmitted by the waveguide is scattered in a direction with a proximal component.

9. A waveguide as in claim 1 which is designed as a guide for visible radiation.

10. A waveguide as in claim 9 wherein said waveguide is formed of one of glass and quartz.

11. A waveguide as in claim 9 wherein said scatter elements comprise gas-filled glass beads.

12. A waveguide as in claim 1 further comprising a reflecting layer on said distal end.

13. A waveguide as in claim 1 wherein said scatter elements comprise regions of changed refractive index proximate to said distal end.

14. A waveguide as in claim 13 wherein said regions of changed refractive index have dimensions and spacing which are larger than the wavelength of light to be transmitted.

15. A method for manufacturing a waveguide, said method comprising:

providing an optically transparent rod having a distal end formed with a concave surface;

providing a scatter body having a convex surface section with a shape corresponding to the concave surface;

depositing an adhesive onto at least one of said concave surface and said convex surface;

incorporating scatter elements in said adhesive; and fitting said convex surface section against said concave surface section.

16. A method as in claim 15 wherein said scatter elements comprise gas-filled beads.

17. A method as in claim 15 wherein said adhesive is applied to the entire surface of said scatter body, said scatter elements being incorporated in said adhesive on said entire surface of said scatter body.

18. A waveguide as in claim 1 wherein the waveguide has an index of refraction, said circumferential surface being exposed to a medium having an index of refraction which is less than the index of refraction of the waveguide.

* * * * *